United States Patent
Schoelling et al.

(10) Patent No.: US 6,450,985 B1
(45) Date of Patent: *Sep. 17, 2002

(54) TAMPON APPLICATOR

(76) Inventors: Hans Werner Schoelling, Dohlenwegg 11, Ennepetal, 58256 (DE); Helena Engvist, 34C Chicopee Dr., Princeton, NJ (US) 08540

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/594,485

(22) Filed: Jan. 31, 1996

(30) Foreign Application Priority Data

Jan. 31, 1995 (DE) .......................... 195 03 011

(51) Int. Cl.⁷ ............................................. A61F 13/20
(52) U.S. Cl. ........................................................ 604/15
(58) Field of Search .................. 604/11–18, 57–60, 604/285–288

(56) References Cited

U.S. PATENT DOCUMENTS

| | | | |
|---|---|---|---|
| 3,683,759 A | 8/1972 | Voss et al. | |
| 4,302,174 A | 11/1981 | Hinzmann | |
| 4,321,993 A | 3/1982 | Hinzmann et al. | |
| 4,412,833 A | 11/1983 | Wiegner et al. | |
| 4,453,925 A | * 6/1984 | Decker | 604/14 |
| 4,508,531 A | 4/1985 | Whitehead | |
| 4,583,964 A | 4/1986 | Warncke | |
| 4,755,164 A | 7/1988 | Hinzmann | |
| 5,087,239 A | * 2/1992 | Beastall et al. | 604/14 |
| 5,279,541 A | * 1/1994 | Frayman et al. | 604/14 |
| 5,290,501 A | 3/1994 | Klesius | |
| 5,348,534 A | * 9/1994 | Tomaszewski et al. | 604/14 |

FOREIGN PATENT DOCUMENTS

| | | |
|---|---|---|
| FR | 2 536 989 | 12/1983 |
| GB | 2 114 448 | 8/1983 |
| WO | WO 94/10959 | 5/1994 |

* cited by examiner

Primary Examiner—Dennis Ruhl

(57) ABSTRACT

Tampon applicator for feminine hygiene, comprising a cylindrical applicator barrel of paper-like material, having a front end comprising segments which are bent forwards and inward with respect to the longitudinal center axis of the applicator barrel, forming a dome whereby a weakening of the segments is provided for reducing their resistance to a spreading movement of the segments during the pushing out of a tampon from the applicator barrel. The bases of the segments are formed by the front, solid-cylindrical end of the applicator barrel and the weakening of the segments is provided on the inner surface and at an axial distance from the base of the segments. The tampon applicator reduces the ejecting pressure by means of the predetermined breaking lines at the inner surface of each segment while the smooth outside of the segments reduces irritations when in use. Additionally, the invention relates to a process and an apparatus for manufacturing said tampon applicator.

21 Claims, 5 Drawing Sheets

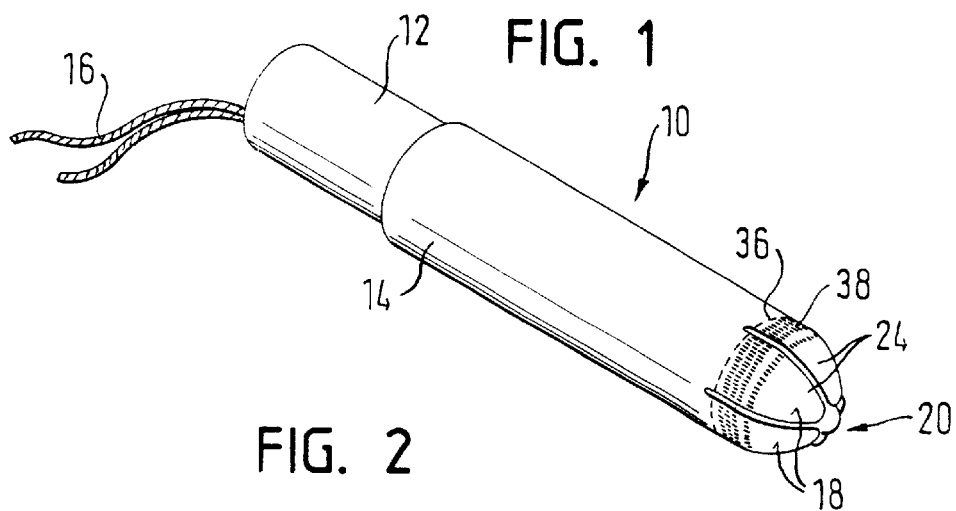
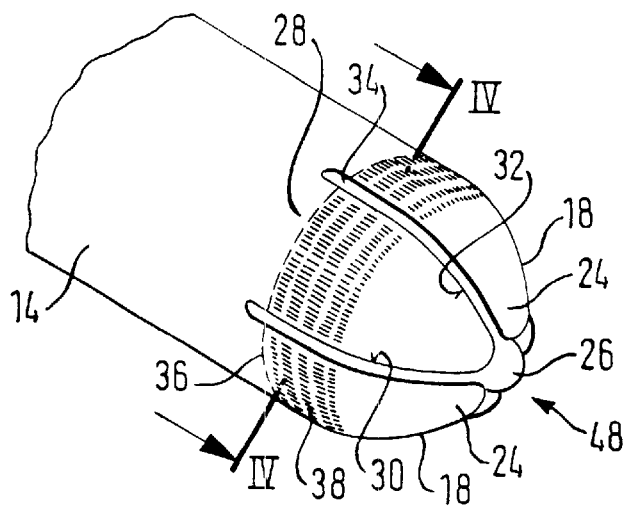
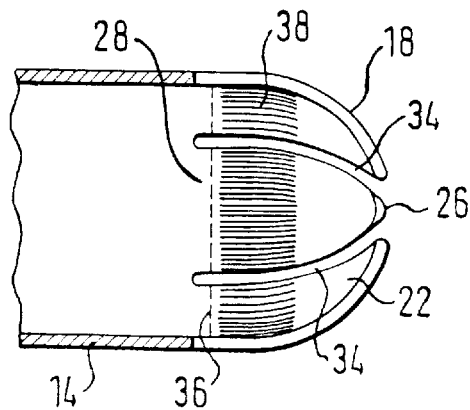
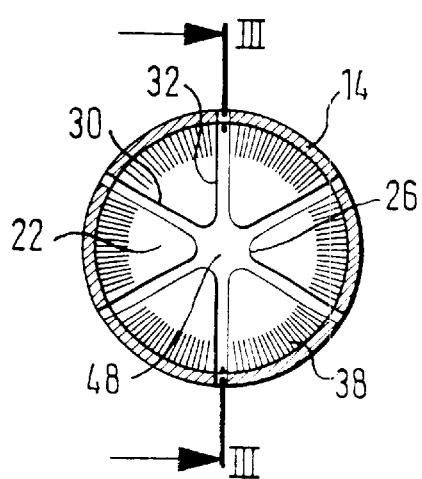

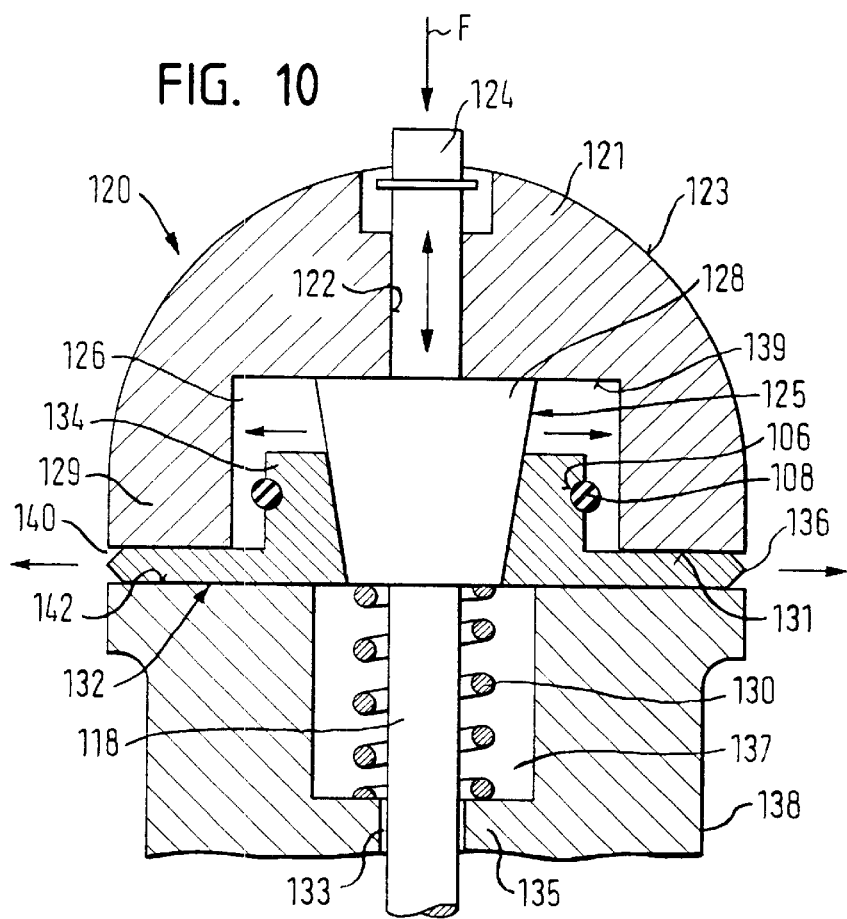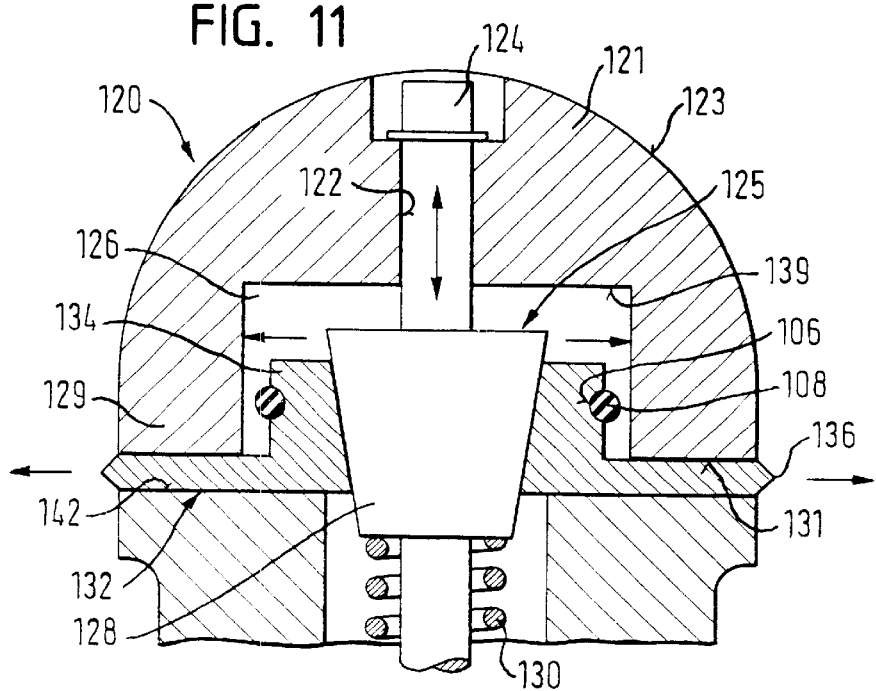

TAMPON APPLICATOR

FIELD OF THE INVENTION

The invention relates to a tampon applicator and to a process for its production and an apparatus for carrying out this process. The tampon applicator has a domed expulsion end with petal-weakening features.

BACKGROUND OF THE INVENTION

Tampon applicators having an applicator barrel and a plunger tube in a telescopic arrangement are commercially available. The applicator barrel generally contains a tampon and at least the front portion of the plunger tube. The barrel and plunger may be formed of a molded, thermoplastic material or a sheet-like material, such as paper and cardboard, coated paper, and the like. Recent developments have included the use of a rounded expulsion end formed of a plurality of curved segments known as petals. Tampons having this general construction are disclosed in Weigner, U.S. Pat. No. 4,412,833, Beastall et al., U.S. Pat. No. 5,087,239, Decker et al., U.S. Pat. No. 4,453,925, Frayman et al., WO 94/10959, Hinzmann, U.S. Pat. Nos. 4,302,174 and 4,755,164, and Hinzmann et al., U.S. Pat. No. 4,321,993.

It is now recognized that designers of such tampon applicators need to reduce the force needed to expel tampons. Thus, Weigner, Beastall et al., and Frayman et al. provide a hinge at the base of the petals. In addition, Frayman et al. provide a plurality of small cuts extending circumferentially from end of the slits and a plurality of circumferential score lines in about the hinge. Decker et al. also provides exterior score lines, claiming that they reduce wrinkling, spring-back and other detriments known in paper applicator tubes. However, these exterior score lines provide potential sources of irritation to users during insertion.

SUMMARY OF THE INVENTION

An object of the invention is to significantly reduce the force necessary to expel the tampon out of the applicator barrel, to increase insertion comfort for the user, and to provide a process and an apparatus which permit an efficient production of the tampon applicator, meeting the requirements demanded of mass production.

The invention achieves these objects by forming rounded petals at the expulsion end of the applicator. The petals are weakened on their inner surface and at an axial distance from the base of the segments where they transition to the cylindrical applicator barrel. This achieves the effect that the bending resistance to a bending out of the segments during ejecting of a tampon arranged in the applicator barrel is significantly reduced, because the width and the curvature of each segment are less at the hinge line running in the circumferential direction than at the segment base. The location of the lines of weakness on the inner surface of each segment at a distance between the hinge line and the free end of each segment further reduces expulsion force. The surface section of each segment lying in front of the hinge line generally opposes the expulsion forces acting outward in response to a bending out of the segments with less of a bending resistance. Thus, partially weakening the wall thickness of the petal material where they are curved to form the domed expulsion end acts to reduce expulsion forces needed. The smooth outer surface of the segments reduces irritation which may otherwise arise during use of the tampon applicator.

In forming the tampon applicator, a plurality of mutually separate, longitudinally extending segments or petals are cut out of at least one end of an applicator blank. The applicator blank is formed of a section of paper-like material. The sides of the blank are joined to produce the cylindrical applicator barrel, and the longitudinally extending segments are shaped to form petals in a dome with a central opening bounded by the front ends of the petals. A hinge line may be formed into the blank before it is formed into the cylindrical applicator barrel, or it may be formed in the formed applicator barrel. The hinge line is spaced toward the segment ends, away from their base where they transition to the cylindrical applicator barrel. At the same time, lines of weakness, extending substantially in the longitudinal direction of the applicator are formed in the inner surface of the petals, spaced toward the segment ends and separated from the circumferential hinge line.

An apparatus useful to form the tampon applicator and to practice the above process includes a stamping and notching apparatus. This stamping and notching apparatus has (a) a stamping head with a convex end face; (b) an outer die with a cylindrical recess and a concave base; and (c) notching jaws. The notching jaws are located in the stamping head and can be moved back and forth radially with respect to the longitudinal center axis of the stamping head by means of an actuating device. The notching jaws have notching edges which are arranged in a plane directed perpendicularly with respect to the main axis of the stamping head at angular intervals on an imaginary circle for forming hinge lines on the inner surface of triangular segments of an applicator barrel.

BRIEF DESCRIPTION OF THE DRAWING

The invention is explained in more detail below with reference to the diagrammatic drawing of an exemplary embodiment of a tampon applicator and of an apparatus for producing the same, in which:

FIG. 1 shows a perspective view of a two-part tampon applicator according to the invention;

FIG. 2 shows the front end of an outer barrel of the tampon applicator in FIG. 1 in an enlarged, broken-away representation;

FIG. 3 shows a longitudinal central section according to line III—III in FIG. 4, in partially broken-away representation, with a view of the inner surface of the applicator barrel;

FIG. 4 shows a view of the inner surface of the front end of the applicator barrel according to crosssection IV—IV in FIG. 2;

FIG. 10 shows a second embodiment of a stamping punch in the position of rest, in a longitudinal central section; and FIG. 11 shows the stamping punch according to FIG. 10 in the notching position, in partially broken-away representation.

DETAILED DESCRIPTION OF THE INVENTION

In FIG. 1 there is shown a tampon applicator 10, which is composed of a tubular slide 12 and a substantially cylindrical applicator barrel 14. The slide 12 and/or the applicator barrel 14 preferably are formed of paper or a paper-like material. If appropriate, they may, also be produced from plastic-coated paper, or even a sheet of plastic, preferably biodegradable plastic.

Figure 6:
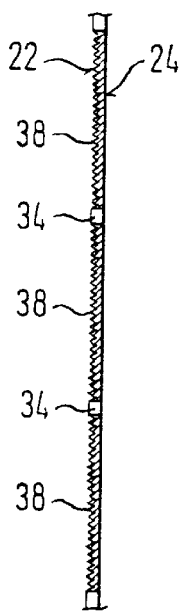
FIG. 6 shows a cross-section VI—VI through regions of weakness of the segments in FIG. 5 on an enlarged scale.

The applicator barrel 14 surrounds a tampon (not shown) for feminine hygiene of liquid-absorbing fibrous material. A withdrawal string 16 of the tampon hangs out of the rear end of the slide 12. At the front end of the applicator barrel 14 there are arranged a plurality of generally triangular segments 18, which are bent forwards and inward symmetrically with respect to the longitudinal center axis of the applicator barrel 14 to give a front, convex, preferably hemispherical, dome 20. Each segment 18 has an inner surface 22 (FIGS. 3 to 7), an outer surface 24 (FIGS. 1, 2 and 6), a rounded-off tip 26, a base 28 (FIGS. 2, 5 and 7) and opposite, rounded-off side edges 30, 32. The side edges 30, 32 of each segment 18 are independent of the side edges of neighboring segments 18 and separated, according to FIG. 5, by slits 34, which extend from the tip 26 of each segment 18 as far as the base 28 of the segments 18. While the slits 34 are shown as having a noticeable width, this width may be minimized to reduce the likelihood of catching and nipping body tissue during insertion and use. This base 28 of the segments 18 is formed by the front, solid-cylindrical end of the applicator barrel 14. The tips 26 of the segments 18 bound a front, central opening 48 of the applicator barrel 14. The diameter of this opening 48 may be, for example, 5 mm (FIG. 4).

A weakening of the segments 18 is provided on their inner surface for reducing their resistance to a spreading movement of the segments 18 during the pushing out of a tampon from the applicator barrel 14, which is designed in a special way, according to the invention, and is described in more detail below.

This weakening of each segment 18 on its inner surface 22 comprises on the one hand at least one hinge line 36, which in each case extends in the circumferential direction of the applicator barrel 14. According to FIGS. 2 to 6, each hinge line 36 of the segments 18 is arranged at an axial distance "a" before the base 28 of the segments 18, which distance should lie in the range of in each case 2 to 6 mm and in the present exemplary embodiment is preferably 3.5 mm. The segments 18 have at their base 28 a width of in each case 8.8 mm. According to FIG. 5, the length of each hinge line 36 notched into the inner surface 22 of each segment 18 is made less than the width of each segment 18 and is arranged symmetrically with respect to the longitudinal axis of each segment 18. In the present case, the two ends of each hinge line 36 lie at a distance "d" of, for example, 1 mm before the nearest side edge 30, 32 of each segment 18. The length of each hinge line 36 is 6.24 mm. The length of the segments 18 between their hinge line 36 and tip 26 is between 7 mm and 12 mm, in the present exemplary embodiment preferably 10.735 mm.

On the other hand, the weakening of the segments 18 on their inner surface 22 is provided by lines of weakness 38, which begin in each case at a small distance "b" from the side of the hinge line 36 of each segment 18 facing towards the tip 26 of each segment 18 and extend from there over a partial section of the length of each segment 18.

Figure 5:
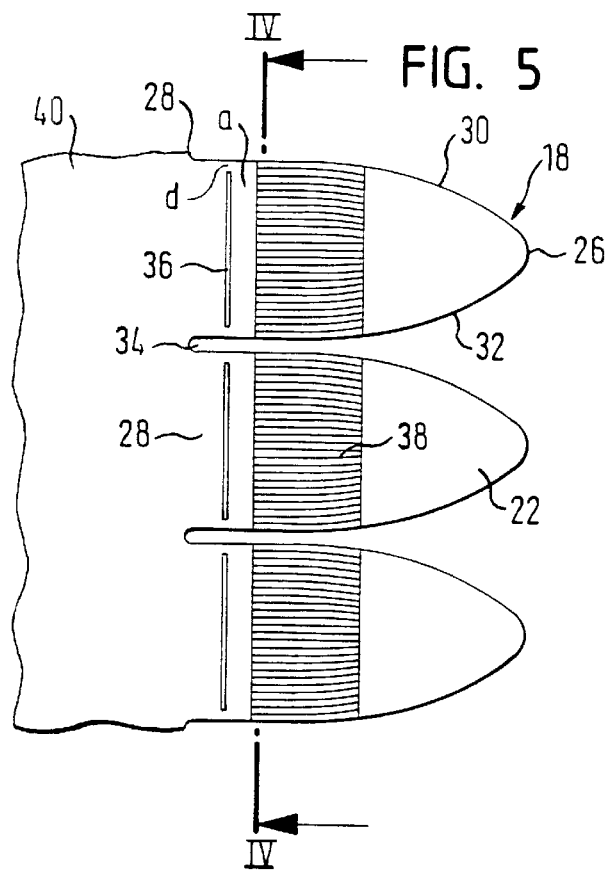
FIG. 5 shows a plan view of the inner surface of a developed projection of an applicator barrel with punched-out segments, in partially broken-away representation.
Figure 5A:
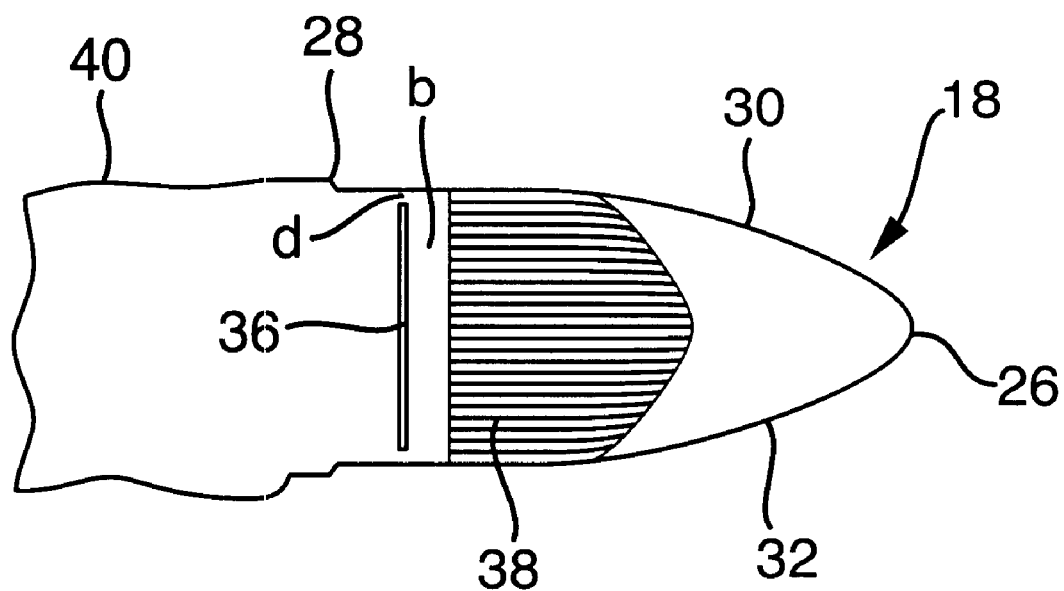
FIG. 5a shows a plan view of the inner surface of a single segment, similar to FIG. 5, according to an alternative embodiment of the invention.

In the partially broken-away plan view according to FIG. 5 there is illustrated the inner surface 22 of a developed projection of the applicator barrel 14 of an initially rectangular section of length 40 of paper-like material having a thickness of 0.3 mm to 0.5 mm, preferably 0.35 mm to 0.40 mm. This section of length 40 may have an overall length of 43.7 mm and an overall width of 152 mm, the segments 18 being provided on its narrow sides. All the lines of weakness 38 are aligned approximately towards the tip 26 of each segment 18 and have an approximately equal length. As a consequence, from the longitudinal center of each segment 18 towards its side edges 30, 32, the lines of weakness 38 run ever more parallel to the side edges 30, 32. A central line of weakness 38 of each segment 18 is preferably arranged exactly on the longitudinal center line of the segment 18. As a departure from the present exemplary embodiment, the lines of weakness 38 of each segment 18 may also be aligned parallel to one another. Furthermore, the lines of weakness 38 may be made increasingly longer towards the center of each segment 18 as shown, for example, in FIG. 5a. The lines of weakness 38 are preferably 2.5 to 6.5 mm long. Particularly preferred is a length of the lines of weakness 38 of 4 mm. The lines of weakness 38 advantageously have a spacing of 0.5 mm×300. The cross-section of the lines of weakness 38 is V-shaped, the angle of the V leg being 35°. The greatest clear width of the V-shaped lines of weakness 38 is 0.5 mm with a depth of penetration into the paper-like material of approximately ⅔ of its thickness.

The inner and outer radii of curvature of the dome 20 formed by the segments 18 lie in the range between 6 and 9 mm. As a rule, three different dome sizes with outer radii of curvature of 6.65, 7.65 and 8.65 mm, respectively, and inner radii of curvature of 6.3, 7.25 and 8.25 mm, respectively, are preferred in the case of tampon applicators with barrels of different diameters for different tampon sizes.

Preferably, both the stamped lines of weakness 38 and the hinge lines 36 are provided on the inner surface 22 of each segment 18 to maintain the smooth, outer surface of the segments 18. This allows easier insertion of the tampon applicator 10 into the body cavity. In addition, the arrangement of the hinge lines 36 separated axially from and between both the base 28 and the lines of weakness 38 offers the advantage of reducing the deformation resistance of each segment 18 during pushing out of a tampon contained in the applicator barrel 14 into the body cavity. The width and the curvature of the segments 18 are reduced at the hinge lines 36 and lines of weakness 38 with respect to the segment base 28 and the bending moment is reduced because of the weakening of the segments 18 on their inner surface. This occurs since the bending forces necessary for spreading apart the segments 18 during pushing out of the tampon from the applicator barrel 14 do not have to be applied at the beginning of the pushing out of the tampon, but essentially only when the front end of the tampon has been advanced approximately one quarter to one third of the length of the segments.

Figure 7:
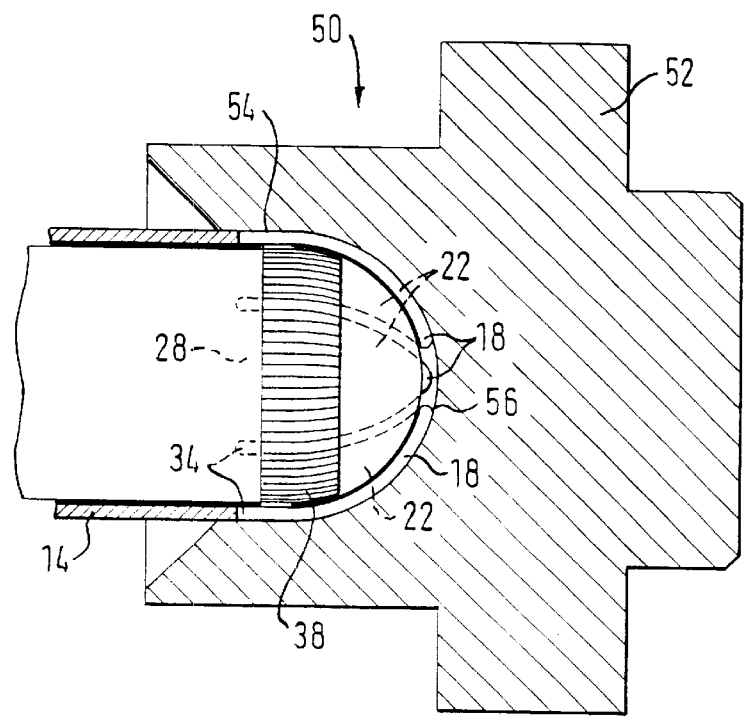
FIG. 7 shows a longitudinal section through an outer die of a combined notching and stamping apparatus with an applicator barrel arranged therein after stamping of the same.

Although according to FIG. 5 the lines of weakness 38 and hinge lines 36 may be impressed or notched into the inner surface 22 of the segments 18 at the same time as or step by step before or after the punching out of the said segments 18, according to FIG. 7 there is shown an outer die 50 of a stamping and notching apparatus according to the invention with an axial, cylindrical recess 54, the diameter of which corresponds approximately to the outside diameter of the applicator barrel 14. Furthermore, the outer die 50 has a concave, preferably hemispherical, base 56 for receiving the triangular segments 18 at the front end of the applicator barrel 14. In the recess 54, the inner surface 22 of an applicator barrel 14 can be seen in longitudinal central section after the stamping of the lines of weakness 38.

Figure 8:
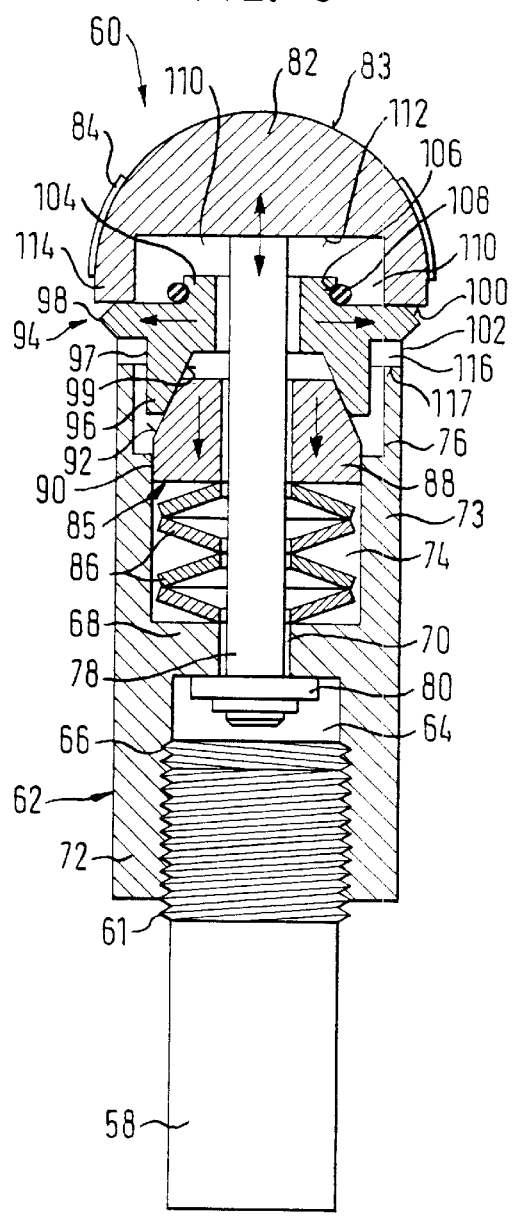
FIG. 8 shows a first embodiment of a stamping punch of the notching and stamping apparatus in a starting position or position of rest in longitudinal central section.
Figure 9:
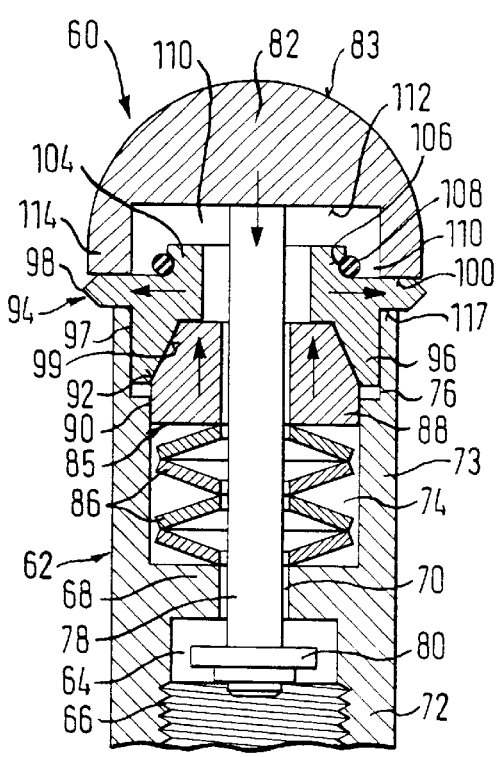
FIG. 9 shows the stamping punch according to FIG. 8 in the working position.

As a further part of this stamping and notching apparatus, for stamping the lines of weakness 38 and for notching the hinge lines 36, a first embodiment of a stamping punch 60 is shown in FIGS. 8 and 9 and a second embodiment of a stamping punch 120 is shown in FIGS. 10 and 11.

According to FIGS. 8 to 11, in the case of both embodiments of the stamping and notching apparatus, the stamping punch 60; 120 is equipped with a stamping head 82; 121, the diameters of which largely correspond to the inside diameter of the applicator barrel 14 and its convex, preferably hemispherical end face 83; 123 of the interior shape of the dome 20 of the applicator barrel 14 in FIG. 1. The outer surface of the stamping heads 82; 121 is partially provided with a knurling 84 which extends over its circumference and, for the sake of simplicity, is shown only in FIG. 8.

The stamping punches 60, 120 are in each case provided with a plurality of circle-sector-like notching jaws 94; 132, the angle at circumference of which is 60° and consequently corresponds to a total number of six segments 18. The notching jaws 94; 132 can be moved back and forth radially with respect to the longitudinal center axis of the stamping head 82; 121 by means of an actuating device 85; 125 and are provided on the outside with notching edges 98; 136, which are arranged in a plane directed perpendicularly with respect to the main axis of the stamping head 82; 121 at angular intervals on an imaginary circle for indenting the hinge lines 36 on the inner surface 22 of the triangular segments 18 of an applicator barrel 14.

The actuating device 85; 125 for the notching jaws 94; 132 in each case comprises a spreading cone 88; 128, which is mounted axially displaceably in the stamping punch 60 and 120, respectively. The notching jaws 94; 132 have spreading segments 96; 134 which bear against the spreading cone 88; 128 radially movably with respect to the main axis of the latter. If the stamping head 82; 121 encounters resistance when entering the outer die 50 in FIG. 7 on the curved base 56 of the cylindrical recess 54 of the said outer die, the notching jaws 94; 132 with their notching edges 98; 136 are moved out by an axial movement of the spreading cone 88; 128 by a certain amount radially beyond the outer circumference of the stamping head 82; 121, in order to notch the hinge lines 36 into the inner surface 22 of the segments 18 of the applicator barrel 14.

According to FIGS. 8 and 9, in the case of the first embodiment of the stamping and notching apparatus, the hemispherical stamping head 82 of the stamping punch 60 is arranged axially movably at a front end of a punching sleeve 62. The knurling 84 extends over the circumference of the end face of the stamping head 82 on a limited section of length of, for example, 5 mm. This knurling 84 comprises stamping ribs, which extend in the axial direction of the stamping head 82, for example over a length of 5 mm, and have a spacing of approximately 0.5 mm ×30°.

The stamping head 82 is fastened on its rear end coaxially on an assembly shaft 78, which extends axially movably through the center of the notching jaws 94, of the spreading cone 88, of a compression spring 86, formed by plate springs, and through a bore 70 in a transverse wall 68 of the punching sleeve 62.

A plate-like widening 80 of the assembly shaft 78 bears against the surface of the transverse wall 68 of the punching sleeve 62 facing away from the stamping head 82 and consequently fixes the axial distance of the stamping head 82 from the punching sleeve 62.

The transverse wall 68 forms the base of a hollow space 74 of the punching sleeve 62, which space has a cylindrical widening 76 at its end facing towards the stamping head 82. The compression spring 86 is arranged in the hollow space 74 of the punching sleeve 62 and is supported with pre-stressing by one end on the transverse wall 68 of the punching sleeve 62 and by the other end on the spreading cone 88.

The spreading cone 88 has a cylindrical section 90 which faces away from the stamping head 82 and is guided axially movably in the cylindrical hollow space 74 of the punching sleeve 62. A frustoconical section 92 extends from this cylindrical section 90 into the cylindrical widening 76 at the front end of the sleeve section 73.

The notching edges 98 of the six notching jaws 94 in each case extend radially with respect to the assembly shaft 78 through six radial grooves 116 in an end rim 102 of the front sleeve section 73 of the punching sleeve 62. In this case, the notching jaws 94 are arranged in the position of rest or starting position shown in FIG. 8 at a clear axial distance from a groove base 117 of the grooves 116 and bear with their notching edges 98 against a rear end face 100 of the stamping head 82. In this case, the said clear axial distance between the notching jaws 94 and the groove bases 117 corresponds approximately to the length of the working stroke of the stamping head 82.

The spreading segments 96 of the notching jaws 94 extend partially into the cylindrical widening 76 of the punching sleeve 62. Outer surfaces 97 of the spreading segments 96 run axially parallel with respect to the assembly shaft 78 and are arranged on an imaginary enveloping cylinder at a radial distance from the wall of the cylindrical widening 76 which is made greater than the radial working stroke of the notching jaws 94.

The spreading segments 96 lie with their inner surfaces 99 on an imaginary frustoconical enveloping surface, the cone angle of which corresponds to that of the spreading cone 88, and are supported on the frustoconical section 92 of the spreading cone 88. In this case, opposing end faces of the notching jaws 94 and of the spreading cone 88 are arranged at an axial distance from one another which is made sufficiently large so that the notching jaws 94 can slide axially with their spreading segments 96 onto the spreading cone 88 and thereby be moved into their radially outer notching position according to FIG. 9 when the stamping head 82 in the outer die 50 has reached its stamping position and is thereby displaced against the action of the compression spring 86 by the notching jaws 94 in the direction of the punching sleeve 62.

In FIG. 8, a rod-shaped holder 58 of the stamping head 82 is arranged such that it can be moved back and forth coaxially by elements known per se (not shown) and is provided with an external thread 61. A rear sleeve section 72 of the cylindrical punching sleeve 62 is provided at its rear end, facing towards the holder 58, with a coaxial, cylindrical depression 64 with an internal thread 66, by which the punching sleeve 62 is screwed onto the holder 58 in an axially adjustable manner. The depression 64 is bounded by the transverse wall 68.

The notching jaws 94 are provided on their front surface, facing towards the stamping head 82, in each case with an axial continuation 104. These continuations 104 have on their radial outer surface arcuate grooves 106 which are concentric with respect to the assembly shaft 78. A spring ring 108, for example an o-ring of flexible material, such as rubber, or a garter spring, is inserted in these grooves 106 of the notching jaws 94, extending over the circumference of the continuations 104, in order to hold the notching jaws 94 against the spreading cone 88 under flexible prestressing.

The stamping head 82 is provided on its rear end with an annular space 110, the head wall 112 of which is directed normally with respect to the assembly shaft 78 and is arranged at an axial distance from the continuations 104 of the notching jaws 94. The annular space 110 is surrounded by an annular rim 114, which has the rear, circular end face 100 which, as mentioned, bears against the end face of the notching jaws 94 which faces towards the stamping head 82.

FIG. 9 shows the stamping position of the stamping head 82, which the latter assumes when the stamping punch 60 has reached its end position in the outer die 50. In this stamping position, the notching edges 98 project radially beyond the rear outer rim of the stamping head 82 and therefore notch the hinge lines 36 in each case into the inner surface of the segments 18 of the applicator barrel 14. At the same time, the lines of weakness 38 are impressed into the inner surface 22 of the segments 18 by the knurling 84 of the stamping head 82. It goes without saying that, depending on the type of stamping pattern chosen and the circumferential length of the hinge line 36 for each segment 18, the applicator barrel 14 must be aligned regarding the position of its segments 18 with respect to the stamping head 82 and the notching edges 98.

In FIG. 10 the second embodiment of the stamping punch 120 with the hemispherical stamping head 121 is shown, in the case of which, for the sake of simplicity, the knurling is no longer shown. Through this stamping head 121 there extends a central bore 122, which is widened on the outer surface of the stamping head 121 and opens out on the rear end of the stamping head 121 into a coaxial, cylindrical recess 126. This recess 126 is surrounded by an annular rim 129, which has a rear, circular end face 131.

The stamping head 121 is firmly arranged on the front end of a punching sleeve 138, which has a central, cylindrical, hollow space 137 which, similarly to the punching sleeve 62 in FIGS. 8 and 9, is provided with a transverse wall 135, which has a central bore 133.

Similarly to FIGS. 8 and 9, an assembly shaft 118 is mounted axially movably in the punching sleeve 138 and in the transverse wall 135 of the latter but, in contrast to the first embodiment, forms a unit not only with the actuating device 125 but also with a front push rod 124. In its unactuated position, the push rod 124 passes through the central bore 122 of the stamping head 121, projecting beyond the curved end face 123 of the latter. The length by which the push rod 124 projects beyond the end face 123 is sufficient for the working or notching stroke of the assembly shaft 118 for notching in the hinge lines 36 on the inner surface 22 of the segments 18 of the applicator barrel 14. In contrast to the first embodiment, the truncated spreading cone 128 of the actuating device 125 is widened towards a head wall 139 of the recess 126. A helical compression spring 130 is arranged in the hollow space 137 of the punching sleeve 138, which spring is supported under prestressing by its one end on the transverse wall 135 and by its other end on an end face of the spreading cone 128 which faces away from the stamping head 121. As a consequence, in the starting position shown in FIG. 10, the spreading cone 128 is pressed by its front end face against the head wall 139 of the recess 126.

The stamping head 121 is at a certain, unchangeable, axial distance from the punching sleeve 138 of the stamping punch 120, forming radial through-openings 140 for the passing through of the notching jaws 132 between the rear end face 131 of the stamping head 142 and a front end face 142 of the punching sleeve 138.

The spreading segments 134 on the side of the notching jaws 132 which is facing towards the stamping head 121 are provided, in a plane normal with respect to the longitudinal axis of the stamping punch 120, with arcuate grooves 106 for receiving a tension-spring ring 108, by means of which the notching jaws 132 are prestressed radially inward with respect to the longitudinal axis of the stamping punch 120.

Once the outer die 50 according to FIG. 7 is fitted with an applicator barrel 14, the stamping head 121 can be inserted into the outer die 50. The push rod 124 is thereby moved through the front opening 48, bounded by the free ends of the segments 18 of the applicator barrel 14, against the hemispherical base 56 of the outer die 50 and is pressed by the said base axially into the stamping head 121. As a result, the spreading cone 128 spreads the notching jaws 132, so that the spreading segments 134 are moved with their notching edges 136 radially outward in order to provide the inner surface of the segments 18 with the hinge lines 36. The stamping head 121 is provided on its outer surface, similarly to the stamping head 82 in FIGS. 8 and 9, with stamping ribs, which are not shown here. Instead of the stamping ribs, a knurling comprising punctiform studs may also be provided, if appropriate, for producing the region of weakness on the inner surface of the segments 18 of the applicator barrel 14.

The process for producing the tampon applicator 10 comprises the feeding of a longitudinally extending web of paper-like material with a width which is made somewhat greater than twice the length of the finished applicator barrel 14. In this case, the segments 18 are cut continuously or step by step one after the other out of the two longitudinal edges of the web. Thereafter, the web is subdivided into sections of length, the length of which corresponds in each case to the circumferential length of an applicator barrel 14. Thereupon, the sections of length are cut through in the longitudinal center, so that in each case two sections of length 40 are formed in a way corresponding to the developed projection in FIG. 5. Then the front end and rear end of each section of length 40 are joined together by adhesion or heat-sealing to give a cylindrical applicator barrel 14. Subsequently, the segments 18 are shaped to give a hemispherical dome 20 with a central opening 48, bounded by the tips 26 of the segments 18. There are thereby simultaneously impressed into the inner surface 22 and at an axial distance from the base 28 of the segments 18 a hinge line 36, directed in the circumferential direction of the applicator barrel 14, and also lines of weakness 38, extending substantially in the longitudinal direction of the segments 18, on the side of each hinge line 36 facing away from the bases 28.

The simultaneous stamping of the hinge lines 36, running in the circumferential direction of the segments 18, and longitudinally directed lines of weakness 38 on the inner surface of the segments 18 of the applicator barrel 14 takes place between the stamping head 82 or 121 and the outer die 50 by means of the smooth, concave recess 54.

In the case of the two-part tampon applicator described above, the outer barrel may be provided on its inner wall with a radially inwardly projecting ejecting element, known per se, which protrudes through a longitudinal slit of the sleeve-shaped slide and initially bears against the recovery end of a tampon arranged in the slide. When the tampon applicator is put to use, the slide can be pulled out from the outer barrel until behind the recovery end of the tampon, the ejecting element keeping the tampon stationary, so that the latter finally bears against the inner wall of the outer barrel and can subsequently be ejected into the body cavity.

As a departure from the described exemplary embodiment of a two-part tampon applicator with outer barrel and slide, the tampon applicator may, however, also be used as a single barrel. In this case, the withdrawal string of a tampon arranged in the applicator barrel, between the inner wall of the applicator barrel and the approximately cylindrical circumferential surface of the tampon, is led through an opening or a slit in the cylindrical barrel wall in the region of the ejecting end of the applicator barrel, so that the tampon can be inserted into the body cavity by pulling the withdrawal string out from the applicator barrel.

LIST OF REFERENCE NUMERALS

10 Tampon applicator
12 Slide
14 Applicator barrel
16 Withdrawal string
18 Segment
20 Dome
22 Inner surface
24 Outer surface
26 Rounded-off tip (segment)
28 Base
30 Side edge
32 Side edge
34 slits
36 Hinge line
38 Lines of weakness
40 Section of length
48 Opening
50 Outer die
54 Recess
56 Base
58 Holder
60 Stamping punch
61 External thread
62 Punching sleeve
64 Depression
66 Internal thread
68 Transverse wall
70 Bore
72 sleeve section (rear)
74 Hollow space
76 Widening
78 Assembly shaft
80 Plate-like widening (assembly shaft)
82 Stamping head
83 End face (stamping head)
84 Knurling
85 Actuating device
86 Compression springs (prestressing device)
88 Spreading cone
90 Cylindrical section
92 Frustoconical section
94 Notching jaws
96 Spreading segments
98 Notching edges
100 Rear end face
102 End rim
104 Axial continuation
106 Arcuate grooves
108 Spring ring
110 Annular space
112 Head wall
114 Annular rim
116 Radial grooves
117 Groove bases
118 Assembly shaft
120 Stamping punch
121 Stamping head
122 Bore
123 End face
124 Push rod
125 Actuating device
126 Recess
127 Conical face
128 Spreading cone
129 Annular rim
130 compression spring
131 Rear end face
132 Notching jaws
133 Bore
134 Spreading segments
135 Transverse wall
136 Notching edges
137 Hollow space, central, cylindrical
138 Punching sleeve
139 Head wall
140 Through-openings
142 End face

What is claimed is:

1. Tampon applicator for feminine hygiene, comprising:
a) a cylindrical applicator barrel, having a central longitudinal axis and a front end from which extend a plurality of generally triangular segments which are bent forwards and inward with respect to the longitudinal axis of the applicator barrel, forming a dome, each segment having
   i) an inner surface and an outer surface,
   ii) opposite side edges, the side edges of each segment being independent of the side edges of adjacent segments,
   iii) a tip,
   iv) a base at which the segment is joined to the cylindrical applicator barrel,
   v) a plurality of lines of weakness provided on the inner surface, and
   vi) a hinge line running in the circumferential direction of the applicator barrel,
wherein the hinge line is offset from the base of the segments toward the segment tips, the lines of weakness are offset from the hinge line, toward the segment tips, and the lines of weakness consist essentially of lines extending substantially in a direction generally corresponding to the longitudinal axis over a portion of the length of each segment; and b) a plunger telescopically disposed within the applicator barrel.

2. Tampon applicator according to claim 1, wherein the lines of weakness have an equal length.

3. Tampon applicator according to claim 1, wherein the lines of weakness converge toward the tip.

4. Tampon applicator according to claim 1, wherein the lines of weakness are arranged approximately parallel to one another.

5. Tampon applicator according to claim 1, wherein the length of the lines of weakness increases towards a center of said segments.

6. Tampon applicator according to claim 1, wherein the lines of weakness have a length of about 2.5 to 6.5 mm.

7. Tampon applicator according to claim 6, wherein the lines of weakness are about 4 mm long.

8. Tampon applicator according to claim 1, wherein the hinge line is offset from the base of each segment by about 2 to 6 mm.

9. Tampon applicator according to claim 8, wherein the hinge line is offset from the base of each segment by about 3.5 mm.

10. Tampon applicator according to claim 1, wherein opposite ends of the hinge line of each segment are offset from the respective side edge of the respective segment.

11. Tampon applicator according to claim 10, wherein the ends of the hinge line of each segment are offset from the respective side edge by about 1 mm.

12. Tampon applicator according to claim 1, wherein the tips of the segments are rounded-off and define a front, central opening of the applicator barrel.

13. Tampon applicator according to claim 12, wherein the front opening of the applicator barrel has a diameter of about 5 mm.

14. Tampon applicator according to claim 1, wherein the dome formed by the segments has an inner radius and outer radius in the range of about 6 to 9 mm.

15. Tampon applicator according to claim 1, wherein the base of the segments has a width of about 8.8 mm.

16. Tampon applicator according to claim 1, wherein the applicator barrel has a thickness of about 0.3 to 0.5 mm.

17. Tampon applicator according to claim 1, wherein the length of each segment from the base to the tip is about 10 mm.

18. The applicator of claim 1 wherein the applicator barrel is formed from a sheet of material.

19. The applicator of claim 18 wherein the material comprises paper.

20. The applicator of claim 18 wherein the material comprises plastic.

21. Tampon applicator according to claim 1, wherein the hinge line is separated from the base of the segments toward the segment tips.

\* \* \* \* \*